United States Patent [19]

Hein

[11] Patent Number: 5,738,108
[45] Date of Patent: Apr. 14, 1998

[54] SYSTEM FOR MULTI-SITE SKIN TESTING AND COMPONENTS THEREOF

[75] Inventor: Gary L. Hein, Oakley, Ill.

[73] Assignee: Lincoln Diagnostics, Inc., Decatur, Ill.

[21] Appl. No.: 818,218

[22] Filed: Mar. 14, 1997

Related U.S. Application Data

[63] Continuation-in-part of Ser. No. 583,771, Jan. 11, 1996.
[51] Int. Cl.⁶ ............................................. A61B 5/00
[52] U.S. Cl. ............................................. 128/743; 128/744
[58] Field of Search ..................................... 128/743, 744

[56] References Cited

U.S. PATENT DOCUMENTS

| | | |
|---|---|---|
| 2,522,309 | 9/1950 | Simon . |
| 3,556,080 | 1/1971 | Hein . |
| 4,711,247 | 12/1987 | Fishman . |
| 5,396,989 | 3/1995 | Hein . |

*Primary Examiner*—Max Hindenburg
*Assistant Examiner*—Pamela L. Wingood
*Attorney, Agent, or Firm*—Lockwood, Alex, FitzGibbon & Cummings

[57] ABSTRACT

A system for making multi-site skin tests primarily for use by allergists making use of a multi-head applicator and a matching multi-well dipwell tray. The applicator has an elongated handle with arms extending transversely from opposite sides having downwardly extending legs terminating in multi-pointed ends or heads capable of picking up and retaining small quantities of liquid skin-testing substances. The multi-point ends or heads occupy the same plane and are arrayed in a pattern suited for simultaneously making multi-site skin tests. The applicator cooperates with a multi-well dipwell tray with a plurality of dipwells arrayed in patterns which match the pattern in which the multi-pointed ends or heads on the cooperating applicator are arrayed. The volume of testing substance or medicament in a dipwell will equal many times the volume of a single dose or increment that is picked up by one of the multi-pointed ends or heads on an applicator. Both the applicator and dipwell tray have guidance formations thereon whereby the user can readily orient the multi-point pick-up ends or heads on the applicator with the dipwells so that the heads can be readily and accurately lowered into the matching dipwells without damaging the points of the applicator. The handle of the applicator also has formations on it which prevent the applicator from being used wrong-end-to.

10 Claims, 2 Drawing Sheets

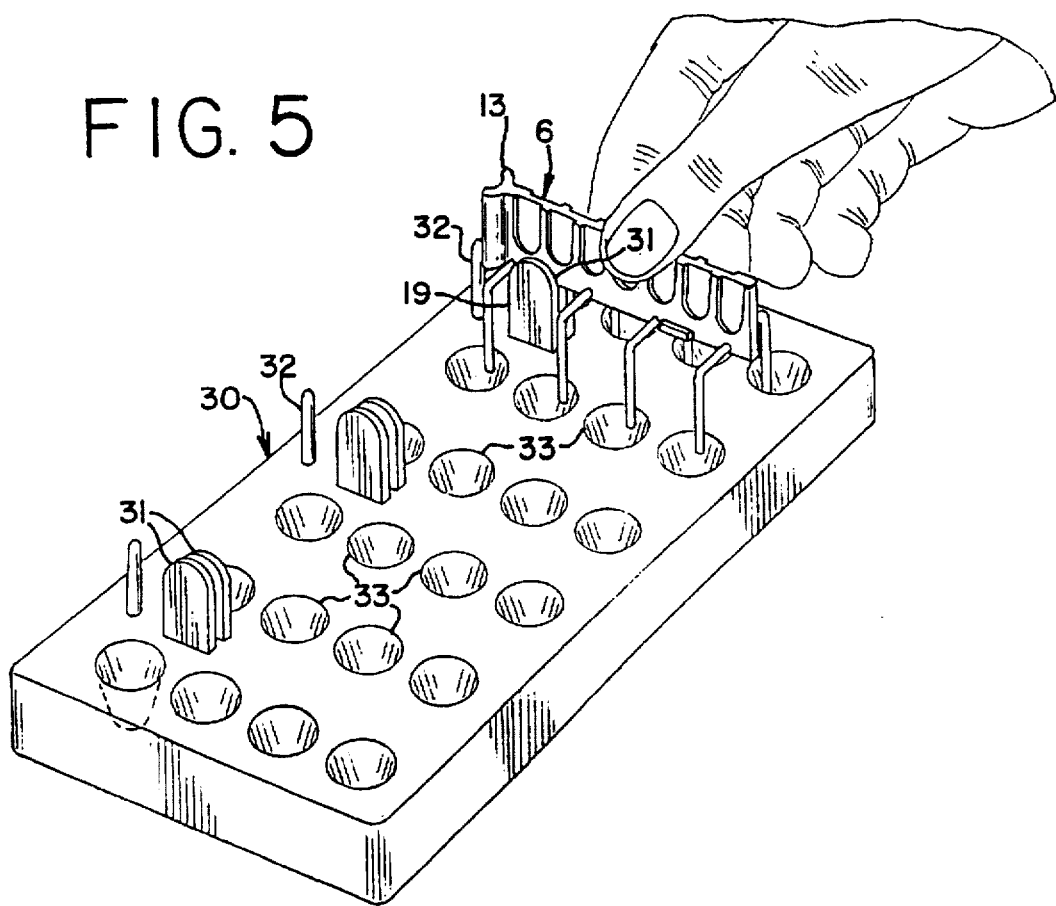
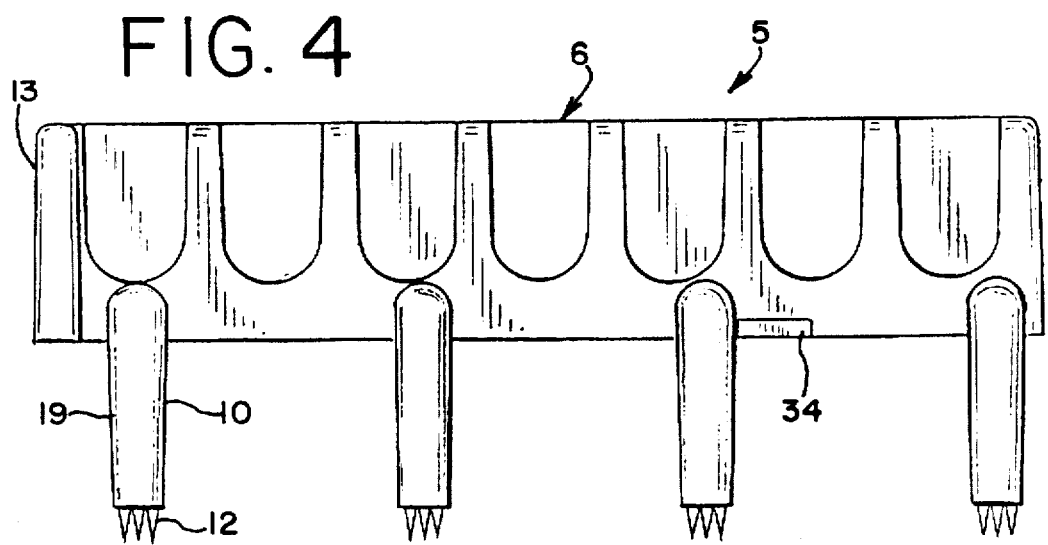

SYSTEM FOR MULTI-SITE SKIN TESTING AND COMPONENTS THEREOF

This application is a continuation-in-part of my co-pending application Ser. No. 08/583,771 filed Jan. 11, 1996.

BACKGROUND OF THE INVENTION

This invention relates generally to an improved system for making multi-site skin tests and to new and improved components used in the system.

Applicant's U.S. Pat. No. 3,556,080 dated Jan. 19, 1971 discloses a system for making multi-site skin tests and components for use in the system. One of the components of the system disclosed in U.S. Pat. No. 3,556,080 is an applicator having a plurality of multi-point, skin-puncturing heads. A second component disclosed in the patent is a form of dipwell tray for use in conjunction with the applicator. The patent teaches loading the tray dipwells with different desired skin testing substances or medicaments such as skin test antigens and allergenic extracts and dipping the applicator heads into the dipwells whereby the multi-point, skin-puncturing heads pick up a load of skin testing substances. According to the patent, the operator then applies the loaded applicator to the skin of a person being tested so that the skin testing substance on each head is introduced at a spaced site on the person's skin. The diameter of each dipwell was of a size to admit the columnar or circular, point base of each head but not large enough to admit the entire head with its annular flange, thereby limiting the points to picking up only two to three loads, which required frequent refilling of the dipwells in order to maintain an adequate fluid level.

While the complete system disclosed in U.S. Pat. No. 3,556,080 was not adopted in practice, the applicator itself, in a commercial form, was adopted and has gone into extensive use by the medical profession. However, the procedure for loading the individual multi-point, skin-puncturing heads has been entirely different from the procedure and method disclosed in the patent since the dipwell tray therein disclosed was not acceptable to the profession because only a few loads could be obtained from each well, requiring frequent refilling of the wells. Then too, it was difficult to place the applicator heads into each well without damaging the points. In the adopted and current procedure the applicator of U.S. Pat. No. 3,556,080 is inverted and the heads are manually loaded, one-by-one, a time-consuming procedure.

According to the invention disclosed in my co-pending application Ser. No. 08/583,771, improvements have been made in both the applicator and the dipwell tray of U.S. Pat. No. 3,556,080 whereby the problems and disadvantages associated with the system disclosed in the patent and the components thereof have been in large measure eliminated. Nevertheless, the possibility remained for the improved applicators disclosed in Ser. No. 08/583,771 to be mis-oriented in use with the improved dipwell tray of Ser. No. 08/583,771. According to the improvements of the present invention, such possibility for mis-orientation has also been eliminated.

Accordingly, the object of the present invention, generally stated, is the providing of an improved system for multi-site skin testing based on the combined use of a novel applicator having multiple skin-puncturing points and a novel dipwell tray for containing an ample supply of skin testing substances to be picked up in small increments when using a series of disposable applicators, and in which the possibility of mis-orientation of an applicator with respect to a dipwell tray has now been eliminated.

Certain other objects and advantages of the invention will become apparent from the following description of preferred embodiments of the invention taken in connection with the accompanying drawings.

BRIEF DESCRIPTION OF THE DRAWINGS

FIG. 4 is a side elevational view of the applicator shown in FIGS. 1–3; and

FIG. 5 is a top perspective view illustrating how the applicator of FIGS. 1–4 is utilized with a dipwell tray such as disclosed in my above-mentioned co-pending application.

Figure 1:
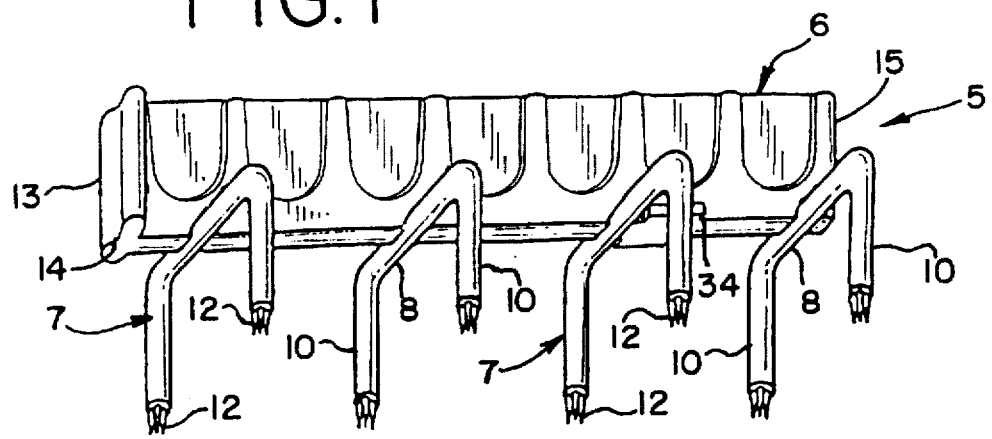
FIG. 1 is a perspective view of an applicator for simultaneously picking up multiple doses or loads of skin testing substances from a dipwell tray and thereafter simultaneously making multiple skin tests on spaced sites on a person's skin embodying the improvements of the present invention.

Referring to the drawings, an applicator is indicated generally at 5 therein comprising an elongated handle 6 from which a plurality of inverted U-shaped limbs 7—7 depend. Each limb 7 comprises a horizontal bight section 8 attached approximately at its mid-point to the underside of the handle 6 and a pair of downwardly extending legs 10—10. The distal ends of all legs 10 lie in approximately the same plane and each end has depending therefrom a multiplicity of skin puncturing points indicated generally at 12—12. For example, the multiplicity of points 12 may take the form of nine pressure-type sharp points clustered closely together so as to create a capillary effect between the points for holding liquid in the interstices or spaces between the points as disclosed in Kravitz U.S. Pat. No. 3,136,314. The disclosure of U.S. Pat. No. 3,136,314 is incorporated by reference herein. The cross sectional size of the legs 10 does not appreciably exceed the cross sectional size of the points 12.

The handle 6 is provided on one end with a guide formation indicated at 13 which extends generally transversely to the handle 6 with a vertically extending concave groove or recess 14 therein. Preferably, the applicator 5 will be integrally molded, such as by injection molding, from a suitable plastic. However, it could be formed from other materials by other methods. By injection molding the applicator 5 from a plastic the cost of these units can be reduced to the point where the applicators are disposable after a single use. The applicators 5 can be sterilized prior to packaging and shipment so that the packages can be opened and the adapters used directly in a sterilized condition.

In FIG. 5, a dipwell tray is indicated generally at 30 which is designed for use with the applicator 5 of FIGS. 1–4. Desirably, the dipwell tray 30 is provided with a cover (not shown) for protecting the contents of the dipwells when the tray is not in use. The tray 30 may be injection molded from plastic so as to have a plurality of dipwells 33—33 arrayed in patterns which correspond to the patterns in which the distal points 12 of the adaptor 5 are arrayed or arranged. Preferably, the shape of the interior of each dipwell is generally conical. This configuration permits each dipwell 33 to have a maximum capacity or volume for a skin testing substance toward the top with a minimized capacity at the bottom whereat only a small residual amount of a skin testing substance is desired. With this configuration, the capacity of each dipwell 33 can be most efficiently and readily utilized with a relatively shallow well. The shallow well enables the use of an applicator with relatively short legs 10 on the U-shaped limbs 7—7. Long legs on the U-shaped limbs would create difficulties in use of the applicator.

The combined length of each leg 10 and its points 12 is such as to be slightly less than the depth of each dipwell 33. This relationship allows the points 12 to be lowered into the dipwells until the horizontal bight sections 8 engage the top surface of the tray 30. Thus, the contents of each dipwell 33 can be substantially entirely utilized. Since the size or diameter of the legs 10 do not exceed or appreciably exceed, the diameters of the pointed ends 12 the ends can be lowered straight down to the bottom of each well without interference with the sidewalls of the wells 33.

Figure 2:
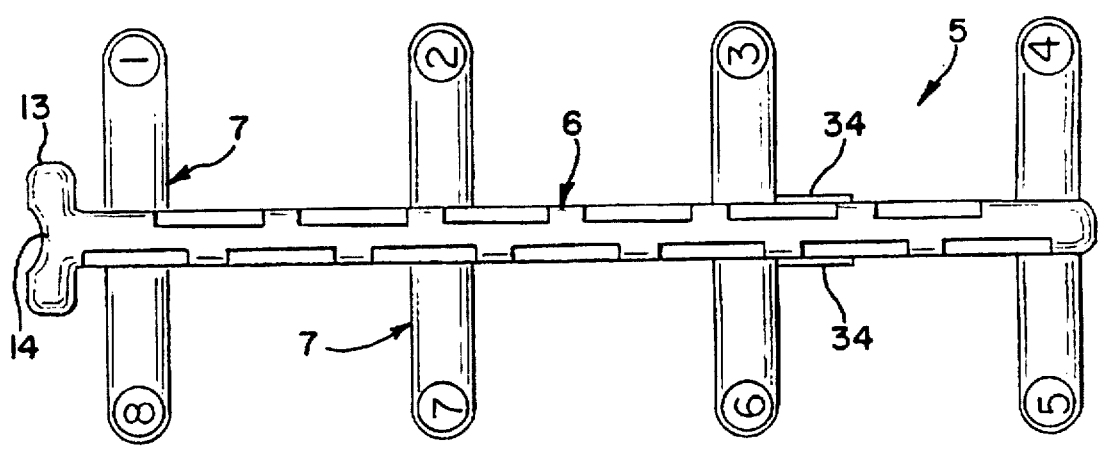
FIG. 2 is a top plan view of the applicator shown in FIG. 1.

It will be noted from FIGS. 1, 2 and 5 that the multiple point distal ends 12—12 of the applicator 5 are arrayed in parallel rows of four each on opposite sides of the handle 6 in a symmetrical pattern. Likewise, the dipwells 33—33 in the tray 30 are arrayed in parallel rows of four each in patterns corresponding to the pattern in which the distal ends 12 are arranged. In use, assuming that the wells 33 are filled with skin testing substances, the objective is to simultaneously dip each of the distal ends 12 of an applicator 5 into a well 33 to substantially the same depth so that the points on the distal ends will pick up a load or dose of the desired medicament from each dipwell. It will be understood that the volume or amount of each dose or increment of medicament picked up is relatively small compared with the volume of the skin testing substance or medicament which each of the wells 33 can hold.

In order to assist the operator or user in quickly and accurately guiding the pointed distal ends 12 of an applicator 5 to substantially the same depths in each of the dipwells 33 and also prevent the distal ends 12 from being inserted into the wrong dipwell 33, both the applicator 5 and the dipwell tray 30 are provided with certain cooperating guidance formations. With respect to the dipwell tray 30, each of the three patterns or sets of dipwells 33 in the tray 30 is provided with an upright orienting pin 32 and a pair of upright parallel tabs 31—31 with the space therebetween aligned with its corresponding guide pin 32. The spacing of the guide tabs 31 is such as to readily receive the handle 6 of an applicator 5 therebetween with little sidewise play between the handle 6 and the tabs 31. The vertical edges 19 (FIGS. 4 and 5) of the tabs 31 nearest to the guide pins 32 are so positioned as to be engaged by the bight or horizontal portion 8 of the adjacent limb 7 as an applicator 5 is lowered into place.

With respect to the applicators 5, each has the one guide formation 13 which assists in accurately guiding each applicator into the proper position and a pair of additional formations 34—34 (FIGS. 2 and 3) which prevent an applicator 5 from being inserted in the dipwell tray in the wrong direction. The guiding formation 13 is integrally formed on one end of the handle 6 so as to have a vertical groove or recess 14 (FIG. 2) which engages one of the upright orienting pins 32.

In FIG. 5, an applicator 5 with its points 12 loaded with medicament is shown being lowered into one of the three sets of dipwells 33. As shown, the handle 6 is being lowered between a pair of the guide tabs 31 while the bight portion or horizontal portion 8 of the limb 7 nearest the formation 13 is beginning to ride down the vertical edges on the tabs 31 as the recess 14 in the formation 13 is sliding down the adjacent guide pin 32. Thus, the applicator handle 6 is guided accurately into position both with respect to the longitudinal positioning of the handle 6 as well as its sidewise positioning.

Figure 3:
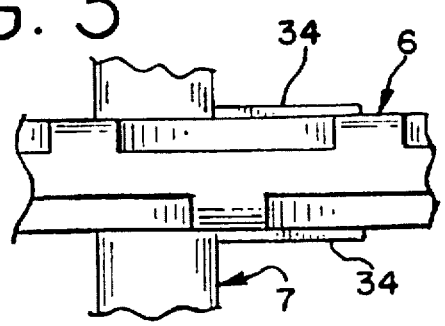
FIG. 3 is a fragmentary plan view on an enlarged scale of the section of the applicator of FIG. 2 located within the broken line circle shown in FIG. 2.

It will be readily apparent to most operators and users, even without first reading the directions, how an applicator 5 should be used so that the points 12 on the lower ends of the limbs 7 enter the proper dipwells 33 so as to pickup thereon loads of the particular medicaments. With only a small amount of practice, a user will come to automatically properly apply an applicator 5 to a dipwell tray 30. However, the possibility exists that an applicator 5 might be inserted or applied wrong-end-to. That is, the applicator 5 shown in FIG. 5 could be rotated 180 degrees so that the end of the handle 6 designated 15 would be placed adjacent an upright guide pin 32. If this were to happen, the points 12 would pick up medicaments from the wrong dipwells 33. In order to prevent such an inadvertent use of an applicator 5, the handle 6 is provided on opposite sides along its bottom edge with the formations 34—34 (FIGS. 2–4). These small rectangular formations protrude from opposite sides of the handle 6 and are so positioned that they will engage the upper ends of the guide tabs 32 if a user attempts to insert an applicator 5 wrong-end-to. The user will then immediately realize his or her error and reverse the direction of the applicator 5 to the correct one.

It will be understood by those skilled in the art that certain changes of an obvious nature may be made in the embodiments of the invention shown and described, and that other embodiments of the invention may be provided without departing from the spirit and scope of the invention as defined in the appended claims.

What is claimed is:

1. In the combination comprising (1) an applicator for simultaneously making multiple skin tests on spaced sites on a person's skin comprising an elongated handle and a plurality of limbs branching outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, and (2) a dipwell tray for holding relatively large volumes of skin test substances in its dipwells to be withdrawn therefrom by said distal ends on said applicator limbs in relatively small increments and having at least one group of dipwells arrayed in a pattern which matches said pattern in which said distal ends are arrayed, the improvements comprising, at least one set of co-operable interengaging orienting formations on said elongated handle and said dipwell tray for orienting said handle in one, and only one, particular relationship with said dipwell tray comprising at least one pair of upstanding formations on said dipwell tray for receiving and orienting said handle therebetween and thereby between parallel rows of said dipwells and at least one additional formation on said handle co-operable with at least one of said pair of upstanding formations to prevent said handle from being inserted in the wrong endwise direction therebetween.

2. In the combination comprising (1) an applicator for simultaneously making multiple skin tests on spaced sites on a person's skin having an elongated handle and a plurality of limbs extending outwardly and downwardly from opposite sides of said handle and terminating in downwardly facing, generally co-planar distal ends having clustered multiple skin-puncturing liquid pick-up points thereon, said distal ends being arrayed in a pattern of parallel rows extending along opposite sides of said handle, and (2) a dipwell tray for holding relatively large volumes of skin test substances in its dipwells to be withdrawn therefrom by said distal ends on said applicator limbs in relatively small increments and having at least one group of dipwells arrayed in a pattern which matches said pattern in which said distal ends are arrayed, at least one set of co-operable interengaging orienting formations on said applicator and dipwell tray which in the correct use of said applicator with respect to said dipwell tray cooperate to correctly orient said distal ends on said applicator with each said group of dipwells so as to facilitate the simultaneous dipping of said distal ends into the skin test substances in each said group of dipwells, the improvement which comprises at least one formation on said handle which will engage one of said orienting formations on said dipwell tray to prevent incorrect orientation of said applicator with respect to said dipwell tray.

3. In the combination of claim 2, one of said co-operable interengaging orienting formations on said applicator and dipwell tray comprising a pair of upstanding spaced parallel tabs positioned on the dipwell tray to receive therebetween said applicator handle and to be engaged by said at least one formation on said handle which will engage one of said orienting formations on said dipwell tray to prevent incorrect use of said applicator with respect to said dipwell tray.

4. In the combination of claim 3, formations projecting from opposite sides of said handle positioned thereon so as to engage said spaced parallel tabs and prevent incorrect use of said applicator with respect to said dipwell tray.

5. In the combination of claim 4, said formations projecting from opposite sides of said handle being in the form of integral strips of handle material extending along the bottom edge of said handle.

6. The applicator called for in claim 1.

7. The applicator called for in claim 2.

8. The applicator called for in claim 3.

9. The applicator called for in claim 4.

10. The applicator called for in claim 5.

\* \* \* \* \*